(12) United States Patent
Wang et al.

(10) Patent No.: US 6,289,291 B1
(45) Date of Patent: Sep. 11, 2001

(54) STATISTICAL METHOD OF MONITORING GATE OXIDE LAYER YIELD

(75) Inventors: Mu-Chun Wang, Hsinchu Hsien; Kuan-Yu Fu, Hsinchu, both of (TW)

(73) Assignee: United Microelectronics Corp., Hsinchu (TW)

( * ) Notice: Subject to any disclaimer, the term of this patent is extended or adjusted under 35 U.S.C. 154(b) by 0 days.

(21) Appl. No.: 09/213,198

(22) Filed: Dec. 17, 1998

(51) Int. Cl.$^7$ .............................. G01N 37/00; G06F 19/00
(52) U.S. Cl. .................. 702/82; 702/84; 702/181
(58) Field of Search .................. 702/34, 35, 58, 702/81–83, 84, 117–119, 179, 185, 181–183; 700/121; 438/17, 462, 770

(56) References Cited

U.S. PATENT DOCUMENTS

| | | | |
|---|---|---|---|
| 3,889,355 | * 6/1975 | Aronsatein et al. | 29/25.01 |
| 5,444,000 | * 8/1995 | Ohkubo et al. | 438/6 |
| 5,638,006 | * 6/1997 | Nariani et al. | 324/765 |
| 6,014,034 | * 1/2000 | Arora et al. | 324/769 |

* cited by examiner

Primary Examiner—Patrick Assouad
Assistant Examiner—Manuel L. Barbee
(74) Attorney, Agent, or Firm—Thomas, Kayden, Horstemeyer & Risley, LLP

(57) ABSTRACT

A statistical method of monitoring the yield of a gate oxide layer. A voltage is applied to first test keys and second test keys to build curves showing relationship between failure distribution and charge density, wherein each of the first test keys has a first oxide area and each of the second test keys has a second oxide area. A yield of the first test keys and a yield of the second test keys up to a charge density can be obtained. The yields of the first test keys and the second test keys have a relationship as an equation of area. To obtain a yield of small test keys, a yield and area of large test keys are imported into an equation. According to operating the equation, the yield of a small gate oxide is obtained.

4 Claims, 3 Drawing Sheets

STATISTICAL METHOD OF MONITORING GATE OXIDE LAYER YIELD

BACKGROUND OF THE INVENTION

1. Field of the Invention

The invention relates in general to a method of evaluating semiconductor circuit yield, and more particularly to a statistical method of evaluating gate oxide layer yield.

2. Description of the Related Art

In the fabrication process of semiconductor devices, wafer acceptance testing (WAT) is often carried out to check gate oxide layer failure distribution of a transistor on a wafer. The method is provided by forming a number of test keys around a particular die on the wafer to perform testing. These test keys are formed on scribe lines between neighboring dies, and are electrically connected to external components, devices, or testing devices via bonding pads. A module of the test keys is selected for testing different device characteristics such as threshold voltage $V_{TH}$ and saturation current $I_{DSAT}$, etc. Whether the test keys fails or not can be detected by measuring a current signal while applying a voltage to the test keys. The yield of the module is N/M, where the module comprises M test keys and there are N keys that have not failed after testing.

FIG. 1 is a top view showing a conventional wafer structure. In FIG. 1, a number of rectangular dies 12 are formed on a wafer 10. Scribe lines 14 are formed with a set of vertical lines perpendicularly intersecting with a set of horizontal lines. The dies 12 are isolated from each other by these scribe lines 14. While forming a transistor on a particular die 12, similar structures are formed on the scribe lines 14 for testing. Therefore, a part of the gate oxide layer of the transistor on the particular die 12 also covers the scribe lines 14. While performing WAT, the part of the gate oxide layer on the scribe lines 14 is electrically connected to an external detector through a bonding pad 16. The WAT result reflects the quality or characteristics of devices formed on each die 12. Therefore, yield of transistors formed on a wafer can be obtained.

As shown in FIG. 2, a gate oxide layer with a large area Ab can be divided into several small areas As. The failure distribution of the large area oxide Ab and the failure distribution of the small area oxide As are in a multiplication relationship. Assume that there are 10 Ab and each Ab is divided into 100 As. As a total, all the large areas Ab are divided into 1000 times the small areas As. If one of the small areas As fails, the large areas Ab also fails. According to the result described above, the failure percentage of Ab will be in general larger that the failure percentage of As. Furthermore, if the failure percentage of a gate oxide layer is X, the yield of the gate oxide layer is (1–X). A formula relates the yield and the area size will be presented later.

Before manufacturing new semiconductor devices, it is necessary to determine the quality of gate oxide layers of the semiconductor devices. A curve of failure distribution versus charge density is obtained to represent the quality of the gate oxide layers. A varying testing voltage is applied on test keys to obtain a charge density of the test keys. When the applied voltages increase, the charge density also increases. With an increase in charge density, the test keys fail one after another.

Many test keys are tested to obtain the curve of failure distribution versus charge density. If a percentage of failure distribution is 0.01%, 10000 test keys must be tested. This methodology requires a lot of testing time and a large sample size to accumulate data to obtain the gate oxide layer yield. The result is that a WAT operation is difficult to perform.

SUMMARY OF THE INVENTION

It is therefore an object of the invention to provide a statistical method to monitor the integrity of gate oxide layers of semiconductor devices in a production line. A lot of testing time and test dies are saved by using the statistical method.

To achieve these and other advantages and in accordance with the purpose of the invention, as embodied and broadly described herein, the invention provides a statistical method of monitoring the yield of gate oxide layers. Failure distributions of gate oxide layers with a large area and of gate oxide layers with a small area are obtained in a stage module process. The degradation trend and the failure distributions have a relationship as a equation of area. The yield and area of a large gate oxide are imported into an equation. According to operating the equation, the yield of a small gate oxide is obtained. The method is convenient and doesn't need to test many test keys so that the testing time and sample size are reduced.

BRIEF DESCRIPTION OF THE DRAWINGS

Other objects, features, and advantages of the invention will become apparent from the following detailed description of the preferred but non-limiting embodiments. The description is made with reference to the accompanying drawings in which.

DESCRIPTION OF THE PREFERRED EMBODIMENT

Figure 1:
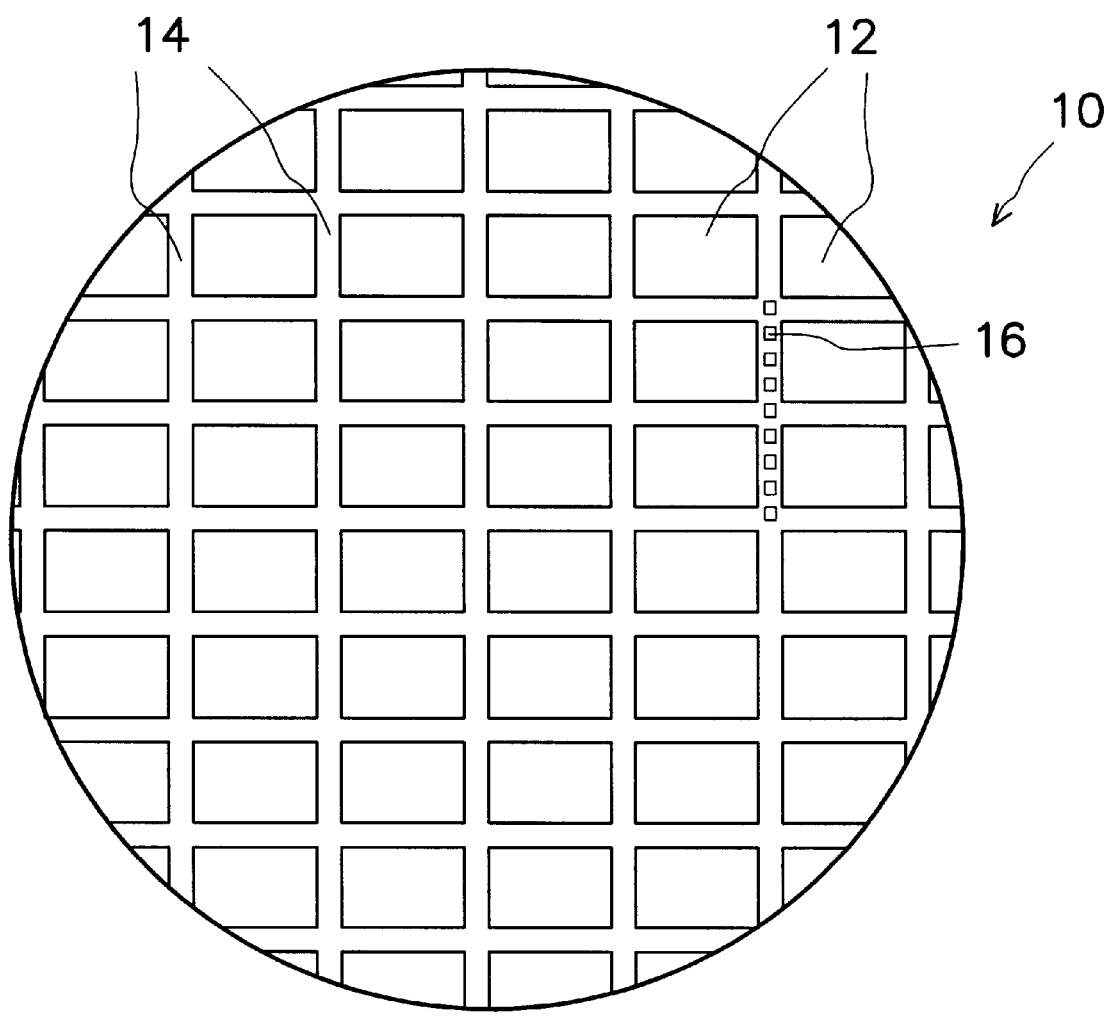
FIG. 1 is a schematic, top view showing a wafer structure.
Figure 2:
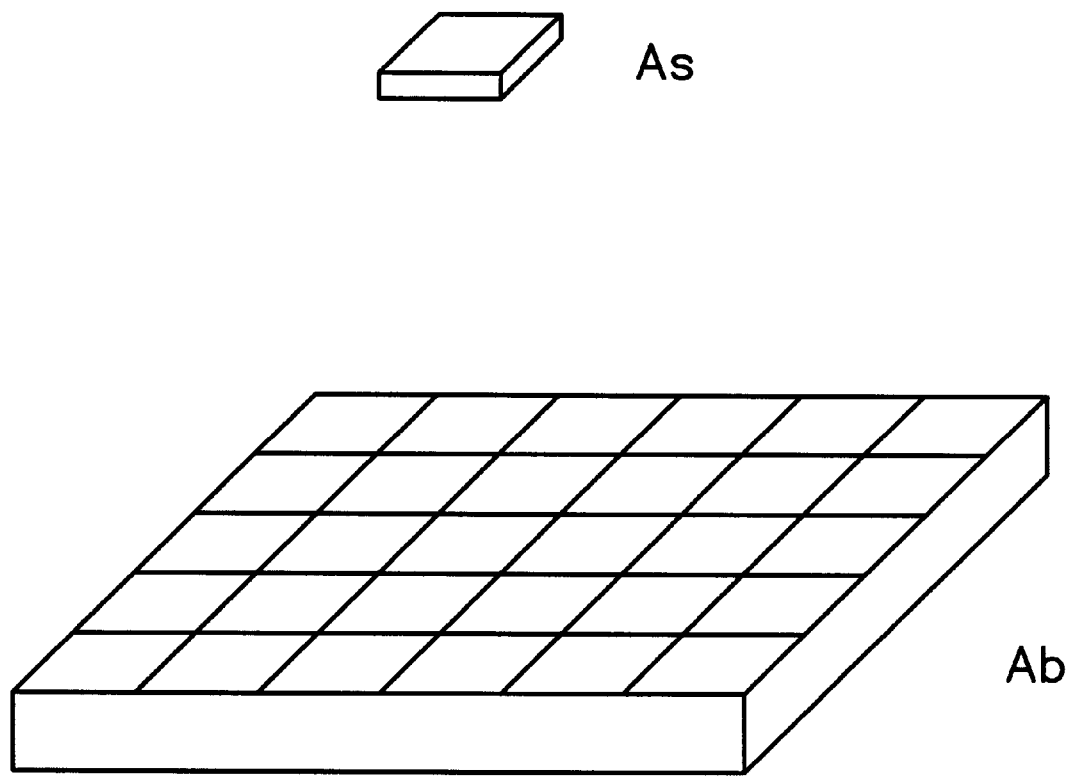
FIG. 2 is a schematic drawing representing the relationship between the yields of a small area gate oxide layer and a large area gate oxide layer.

Before going to a production line, an evaluation of failure distribution of a wafer has to be performed. A scribe line in a wafer consists of first test keys and second test keys. Each of the first test keys has a large area Ab and each of the second test keys has a small area As. The relationship between the large area Ab and the small area As is shown in FIG. 2. Testing voltages (or currents) are ramped up to the first test keys and the second test keys.

Using the 100 first test keys as an example, a voltage (or current) is ramped up to the first test keys. When each of the first test keys fails, the failure distribution of the first test keys is represented by its fail percentage versus the total charge density influence up to the failed point. This establishes the relationship between the failure percentage and the charge-to-breakdown ($Q_{bd}$) of the first test keys, which is termed as failure distribution. The second test keys are tested and observed in a same way as the first test keys, so that the failure distribution can be also established.

Figure 3:
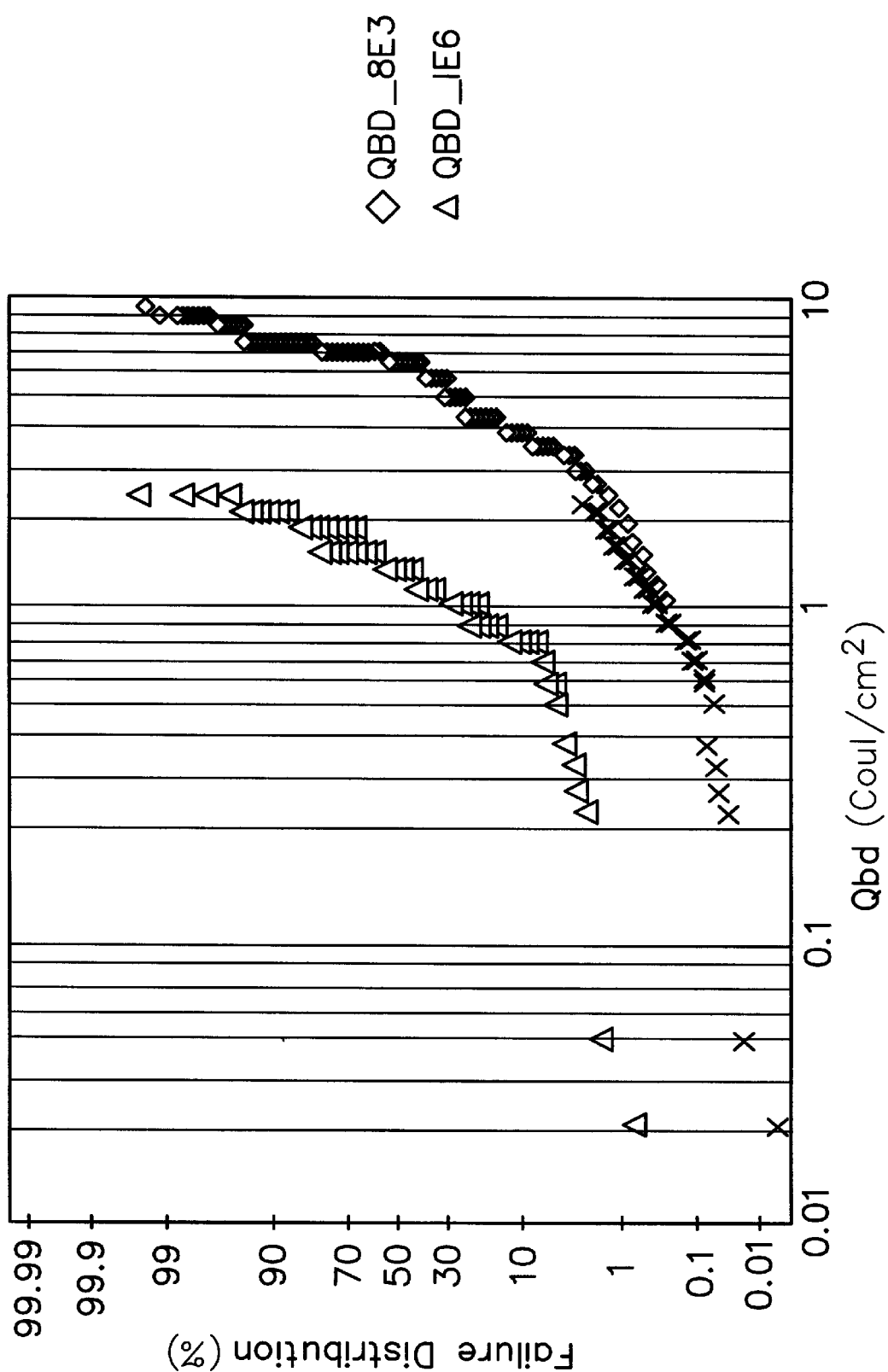
FIG. 3 is a curve diagram showing the oxide yield in relation to a large oxide area and a small oxide area according to one preferred embodiment of this invention.

FIG. 3 is showing the gate oxide failure distribution against charge density of both the first test keys and the second test keys. The relationships between failure distributions and $Q_{bd}$ of the first test keys are represented by symbols △. A curve QBD_1E6 is drawn along these points denoted by △. The relationships between the failure distribution and $Q_{bd}$ of the second test keys are represented by symbols ◇. A curve QBD_8E3 is drawn along these points denoted by ◇. Assuming that each of the first test keys has an oxide area of about $1\times10^6$ um$^2$, and each of the second test keys has an oxide area of about $8\times10^3$ um$^2$. One hundred first test keys and one hundred second test keys are tested. As shown in FIG. 3, to reach a same failure percentage, the first oxide area has a lower charge density than the second oxide area. On the other hand, with a same $Q_{bd}$, the number of the second test keys which fail for testing are less than the number of the first test keys which fail. To obtain the failure distribution of more and more test keys of smaller oxide area, a longer time is required.

As shown in figure, the failure percentage is as low as 0.01% of the second test keys at a $Q_{bd}$ which causes the first test keys to have a failure percentage of 1%. To obtain a failure distribution as precise as 0.01%, 10000 of second test keys are required. Therefore, a long testing time is consumed. Moreover, the total sample size of the second test keys is required to obtain the failure distribution curve.

From the curves as shown in FIG. 3, the yield Y of an oxide layer can be presented by an equation (100):

$$Y=1-F=e^{-DA} \tag{100}$$

Wherein F represents failure distribution, D represents defect density and A represents the area of the oxide layer.

According the equation (100), the yields $Y_b(a)$ and $Y_s(a)$ of the first test keys and of the second test keys up to a charge density a can be presented as:

$$Y_b(a)=[Y_s(a)]^{(Ab/As)} \tag{102}$$

Wherein a represents the $Q_{bd}$ of an oxide area of both the first test keys and the second test keys. As represents oxide area of the second test keys. Ab represents oxide area of the first test keys.

As mentioned above, there is a relationship of failure distribution versus charge density $Q_{bd}$ between a wafer with a larger oxide area and a wafer with a smaller oxide area. The relationship is presented as the equation (102). Therefore, by testing several large oxide areas, a higher precision of failure distribution can be derived from the equation (102) instead of performing a test to a great number of test keys with small oxide areas.

Back to the example shown in FIG. 3, 100 first test keys are tested to obtain the curve of QBD_1E6. The yield $Y_b(a)$ can be calculated by substituting the data of the curve QBD_1E6 into the equation (102) obtained from the equation (100) using the data of the curve QBD_1E6. A yield $Y_s(a)$ of the second test keys with small oxide area can be obtained by substituting $Y_b(a)$ into the equation (102). A simulated curve drawn and denoted by symbols x of failure distribution can thus be obtained by converting $Y_s(a)$ into F (the failure distribution) according to the equation (100). The overlap between the curve of test result drawn by symbol ◇ and the curve of the simulated results drawn by symbols x indicates that the equation (102) can precisely predict the yield of test keys with any oxide area as specifically required.

Considering the edge effect, the relationship between a yield of first test keys with a first perimeter and a yield of second test keys with a second perimeter may also be presented as equation (102). That is $$Y_{pb}(a)=[Y_{ps}(a)]^{(Pb/Ps)} \tag{103}$$

As a consequence, the relationship between yield of the first and second test keys is modified as:

$$Y_b'(a)=Y_b(a)\times Y_{pb}(a)=[Y_s(a)]^{Ab/As}\times[Y_{ps}(a)]^{Pb/Ps} \tag{104}$$

Wherein Pb represents total perimeter of the first oxide area, Ps represents total perimeter of the second oxide area, $Y_b'(a)$ represents the yield of Ab and Pb up to the charge density a, $Y_b(a)$ represents the probability for the first oxide area that the structure remains robust up to a, $Y_s(a)$ represents the probability for the second oxide area that the structure remains robust up to a, $Y_{pb}(a)$ represents the probability at the perimeter for the first oxide area that the structure remains robust up to a, and $Y_{ps}(a)$ represents the probability at the perimeter for the second oxide area that the structure remains robust up to a.

For a wafer comprising more than one gate oxide structure such as large area, finger-type and small area, the equation (102) is thus modified by:

$$Y(a)=[Y_{au}(a)]^A\times[Y_{pu}(a)]^P \tag{106}$$

Wherein Y(a) is the yield probability that a gate oxide layer with an arbitrary shape remains robust up to a, A represents an area of the gate oxide, P represents a perimeter of the gate oxide, $Y_{au}(a)$ represents the yield probability of unit area, and $Y_{pu}(a)$ represents the yield probability of unit perimeter.

The invention provides equations to predict the degradation trend and failure distribution of a gate oxide layer. The yield of a small oxide area can be predicted from the yield of a large oxide area so that a testing time is reduced and testing samples are described.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

What is claimed is:

1. A method of monitoring the yield of a gate oxide layer, comprising the steps of:

providing a plurality of first test keys and a plurality of second test keys, wherein each of the first test keys has a first area Ab and each of the second test keys has a second area As;

testing the first test keys to obtain a curve of failure distribution F as a fuction of charge density a;

calculating a yield $Y_b(a)$ of the first test keys from data of the failure distribution F; and substituting the yield $Y_b(a)$ of the first test keys into a equation $Y_b(a)=[Y_s(a)]^{(Ab/As)}$ to obtain a yield of the second test keys $Y_s(a)$;

wherein the yield $Y_b(a)$ is modified by a factor $Y_{pb}(a)$, wherein: $Y_{pb}(a)=[Y_{ps}(a)]^{(Pb/Ps)}$, so that the modified yield $Y_b'(a)$ is:

$$Y_b'(a)=Y_b(a)\times Y_{pb}(a)=[Y_s(a)]^{Ab/As}\times[Y_{ps}(a)]^{Pb/Ps}$$

wherein $Y_b(a)$ represents the yield of the first test keys up to the charge density a;

$Y_b(a)$ represents the probability for the first test keys that the structure remains robust up to a;

$Y_{pb}(a)$ represents the probability at the perimeter for the first test keys that the structure remains robust up to a;

Ab and Pb represent respectively the area and the total perimeter of the first test keys;

As and Ps represent respectively the area and the total perimeter of the second test keys;

$Y_s(a)$ represents the probability for the second test keys that the structure remains robust up to a; and $Y_{ps}(a)$ represents the probability at the perimeter for the second test keys that the structure remains robust up to a.

2. A method of monitoring the yield of a gate oxide layer, comprising the steps of:

providing a plurality of first test keys and a plurality of second test keys, wherein each of the first test keys has a first area Ab and each of the second test keys has a second area As;

testing the first test keys to obtain a curve of failure distribution F as a function of charge density a:

calculating a yield $Y_b(a)$ of the first test keys from data of the failure distribution F; and substituting the yield $Y_b(a)$ of the first test keys into a equation $Y_b(a) = [Y_s(a)]^{(Ab/As)}$ to obtain a yield of the second test keys $Y_s(a)$;

wherein the gate oxide layer comprises more than one structure, and the modified yield Y(a) is:

$$Y(a) = [Y_{au}(a)]^A \times [Y_{pu}(a)]^P$$

wherein

Y(a) is the yield probability that a gate oxide layer with an arbitrary shape remains robust up to a;

A represents an area of the gate oxide;

P represents a perimeter of the gate oxide;

$Y_{au}(a)$ represents the yield probability of unit area; and $Y_{pu}(a)$ represents the yield probability of unit perimeter.

3. A method of monitoring the yield of a gate oxide layer, comprising the steps of:

providing a plurality of first test keys and a plurality of second test keys, wherein each of the first test keys has a first oxide area Ab and each of the second test keys has a second oxide area As;

continually applying a voltage to the first test keys for testing;

recording each data of failure distribution against charge density while each of the first test keys fails until all the first test keys fail;

drawing a curve of each of the recorded data of failure distribution against charge density;

converting the failure distribution into a yield $Y_b(a)$ of the first test keys; and substituting the yield $Y_b(a)$ of the first test keys into a equation $Y_b(a) = [Y_s(a)]^{(Ab/As)}$ to obtain a yield of the second test keys;

wherein the yield $Y_b(a)$ is modified by a factor $Y_{pb}(a)$, wherein: $Y_{pb}(a) = [Y_{ps}(a)]^{(Pb/Ps)}$, so that the modified yield $Y_b'(a)$ is:

$$Y_b'(a) = Y_b(a) \times Y_{pb}(a) = [Y_s(a)]^{Ab/As} \times [Y_{ps}(a)]^{Pb/Ps}$$

wherein $Y_b(a)$ represents the yield of the first test keys up to the charge density a;

$Y_b(a)$ represents the probability for the first test keys that the structure remains robust up to a;

$Y_{pb}(a)$ represents the probability at the perimeter for the first test keys that the structure remains robust up to a;

Ab and Pb represent respectively the area and the total perimeter of the first test keys;

As and Ps represent respectively the area and the total perimeter of the second test keys;

$Y_s(a)$ represents the probability for the second test keys that the structure remains robust up to a; and $Y_{ps}(a)$ represents the probability at the perimeter for the second test keys that the structure remains robust up to a.

4. A method of monitoring the yield of a gate oxide layer, comprising the steps of:

providing a plurality of first test keys and a plurality of second test keys, wherein each of the first test keys has a first oxide area Ab and each of the second test keys has a second oxide area As;

continually applying a voltage to the first test keys for testing;

recording each data of failure distribution against charge density while each of the first test keys fails until all the first test keys fail;

drawing a curve of each of the recorded data of failure distribution against charge density;

converting the failure distribution into a yield $Y_b(a)$ of the first test keys; and substituting the yield $Y_b(a)$ of the first test keys into a equation $Y_b(a) = [Y_s(a)]^{(Ab/As)}$ to obtain a yield of the second test keys;

wherein the gate oxide layer comprises more than one structure, and the modified yield Y(a) is:

$$Y(a) = [Y_{au}(a)]^A \times [Y_{pu}(a)]^P$$

wherein

Y(a) is the yield probability that a gate oxide layer with an arbitrary shape remains robust up to a;

A represents an area of the gate oxide;

P represents a perimeter of the gate oxide;

$Y_{au}(a)$ represents the yield probability of unit area; and $Y_{pu}(a)$ represents the yield probability of unit perimeter.

* * * * *